United States Patent
Kaur et al.

(10) Patent No.: US 11,370,987 B2
(45) Date of Patent: Jun. 28, 2022

(54) METHOD OF CONTROLLING KINEMATIC VISCOSITY OF POLYALPHAOLEFIN

(71) Applicant: Indian Oil Corporation Limited, Mumbai (IN)

(72) Inventors: Sukhdeep Kaur, Faridabad (IN); Usharani Sahoo, Faridabad (IN); Gurmeet Singh, Faridabad (IN); Naresh Pappu, Faridabad (IN); Jai Narayan Pandey, Faridabad (IN); Shobhashankar Kumhar, Faridabad (IN); Gurpreet Singh Kapur, Faridabad (IN); Deepak Saxena, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 17/229,088

(22) Filed: Apr. 13, 2021

(65) Prior Publication Data
US 2021/0317380 A1    Oct. 14, 2021

(30) Foreign Application Priority Data
Apr. 14, 2020    (IN) .............................. 202021016105

(51) Int. Cl.
| C10M 107/10 | (2006.01) |
| C07C 2/06 | (2006.01) |
| C08F 110/14 | (2006.01) |
| C10N 20/02 | (2006.01) |

(52) U.S. Cl.
CPC ............. *C10M 107/10* (2013.01); *C07C 2/06* (2013.01); *C08F 110/14* (2013.01); *C10M 2205/0285* (2013.01); *C10N 2020/02* (2013.01)

(58) Field of Classification Search
CPC ........... C08F 110/14; C08F 10/14; C08F 4/14
USPC ........................................................ 585/532
See application file for complete search history.

(56) References Cited

U.S. PATENT DOCUMENTS

| 4,031,159 A | 6/1977 | Mandai et al. |
| 4,041,098 A | 8/1977 | Loveless |
| 4,219,691 A | 8/1980 | Mandai |
| 5,196,635 A | 3/1993 | Kumar et al. |
| 5,451,704 A | 9/1995 | Ho et al. |
| 5,463,158 A | 10/1995 | Goledzinowski et al. |
| 6,395,948 B1 * | 5/2002 | Hope .................. C07C 2/26 585/510 |
| 7,104,465 B2 | 9/2006 | Persoons et al. |
| 7,259,284 B2 | 8/2007 | Hope et al. |
| 7,547,811 B2 * | 6/2009 | Kramer ............... C10G 50/02 585/510 |
| 7,550,640 B2 | 6/2009 | Surana et al. |
| 7,880,047 B2 | 2/2011 | Knowles et al. |
| 8,067,652 B2 | 11/2011 | Bburton et al. |
| 8,207,390 B2 | 6/2012 | Wu et al. |
| 8,865,959 B2 * | 10/2014 | Patil .................. C10G 50/02 585/517 |
| 9,708,549 B2 | 7/2017 | Gee et al. |
| 2001/0041818 A1 | 11/2001 | Bagheri et al. |
| 2004/0030075 A1 * | 2/2004 | Hope .................. C08F 4/14 526/237 |
| 2011/0137091 A1 * | 6/2011 | Yang .................. C08F 10/14 585/10 |
| 2015/0166429 A1 * | 6/2015 | Gee .................. C10G 69/126 585/18 |
| 2015/0183901 A1 * | 7/2015 | Ghosh .............. C08F 110/14 525/338 |

FOREIGN PATENT DOCUMENTS

CN    106957677 A    7/2017

OTHER PUBLICATIONS

Extended European Search Report, dated Aug. 11, 2021, from European Patent Application No. 21168133.3 filed Apr. 13, 2021.
Voelkel, Adam et al., "Chromatographic and non-chromatographic characterization of poly-[alpha]-olefins", Journal of Synthetic Lubrication, vol. 24, No. 2, Jan. 1, 2007, pp. 91-100, XP055829619.
India Examination Report, dated Nov. 16, 2021, from India Patent Application No. 202021016105 filed Apr. 14, 2020.

* cited by examiner

*Primary Examiner* — Ellen M McAvoy
(74) *Attorney, Agent, or Firm* — Workman Nydegger

(57) ABSTRACT

The invention relates to a method of the oligomerization of C6 and above olefin monomer whereby, at a fixed monomer/Al halide mole ratio, polyalphaolefins having desirable kinematic viscosities are prepared by controlling the oligomerization temperature. The oligomerization is carried out in presence of an oligomerizing catalyst comprising of aluminum halide and a promoter, and oligomerizing temperatures of about 10° C. to about 120° C.

11 Claims, No Drawings

METHOD OF CONTROLLING KINEMATIC VISCOSITY OF POLYALPHAOLEFIN

FIELD OF THE INVENTION

The present invention relates to a method of oligomerization of $C_6$ and above olefin monomer to polyalphaolefin (PAO) using aluminum halide as catalyst along with a promoter. More specifically, the present invention relates to a method of controlling the kinematic viscosity of polyalphaolefins by adjusting the oligomerization temperature at fixed monomer/aluminum halide mole ratios.

BACKGROUND OF THE INVENTION

The oligomerization of higher olefins gives polyalphaolefins, which are used as synthetic base oils for lubricant applications. Polyalphaolefins are used in many synthetic products such as lubricants, greases and fluids, and have emerged as essential components in many industries and applications. Polyalphaolefins are specially designed chemicals that are uniquely made from alpha olefins. The increase in polyalphaolefins applications is largely driven by the stability of the polyalphaolefins molecules. This stability, along with a host of other unique performance characteristics, makes polyalphaolefins far superior to mineral oils in a variety of uses.

Efforts to improve upon the performance of polyalphaolefins have been the subject of important research and development in the petroleum industry for several decades. Industrial research efforts on synthetic methods for producing polyalphaolefins exhibiting useful viscosities over a wide range of temperatures, i.e., having an improved viscosity index (VI), while also showing lubricity, thermal, and oxidative stability and pour point equal to or better than mineral oil lubricants.

Polyalphaolefins may be produced by using olefin as the feed and using $BF_3$ and $AlCl_3$ along with promoter as catalyst. The evaluation of polyalphaolefins to various test conditions is carried out only after hydrogenation of polyalphaolefins is performed after oligomerization. In general, polyalphaolefins, in the range of from 4 to 6 cSt, are typically made by oligomerization of 1-decene using a $BF_3$ catalyst and an alcohol promoter.

Traditionally, olefin feed used for oligomerization is 1-octene, 1-decene, 1-dodecene, 1-tetradecene and where possible mixtures also but the preferred olefin is 1-decene.

There are various known methods for forming polyalphaolefins in prior-art documents. Some of them are discussed herein below.

U.S. Pat. No. 9,708,549 describes the method for oligomerizing olefin or for producing polyalphaolefin utilizing catalyst mixtures comprising aluminum halides and an organic liquid carrier where the organic liquid carrier comprises of at least 75 mole % 1,2-disubstituted olefins, trisubstituted olefins, or any combination thereof. This patent teaches that stable liquid solutions can be formed between aluminum halides and an organic liquid carrier which can be prepared in advance of its use and stored for long periods of time.

U.S. Pat. No. 5,196,635 describes the preparation of olefin oligomers by polymerizing one or a mixture of olefins, in the presence of a catalyst prepared by reacting in an organic solvent an aluminum halide and proton donor. The olefin oligomer produced is having a kinematic viscosity of from about 30 to 400 cSt at 100° C.

U.S. Pat. No. 5,463,158 describes a process for the catalytic oligomerization of light olefins, such as ethylene or propylene using a liquid catalyst which comprises a Lewis acid and a Lewis base component which forms with the Lewis acid a melt which is liquid at room temperature. The Lewis acid is a metal halide, such as aluminum trichloride and the Lewis base is an organic salt, such as an organic halide salt containing an N-heterocyclic ring or salts containing fully substituted onium ions.

U.S. Pat. No. 5,451,704 describes a process for the production of hydrocarbon lubricant base stock comprises contacting C2 to C20 alpha-olefin feedstock, or mixtures under heterogeneous oligomerization conditions with $AlCl_3$ anchored on an adsorbent inorganic oxide solid, e.g., silica.

U.S. Pat. No. 4,219,691 describes a process for producing olefin oligomer from olefins having not less than 6 carbon atoms in the presence of a reaction mixture of an aluminum halide and a secondary or tertiary alcohol in equivalent proportions. The olefin oligomers thus obtained have a high kinematic viscosity, a low pour point, a high viscosity index and a good shear stability. It also discloses that even if the reaction ratio of the aluminum halide and the secondary or tertiary alcohol is changed within the above-mentioned range, the kinematic viscosity of the oligomers so obtained is not greatly changed.

U.S. Pat. No. 8,865,959B2 relates to a process to produce a poly alpha-olefin (PAO) comprising: a) contacting one or more C4 to C24 alpha olefin monomers with a metallocene compound, and optionally an activator to produce a low molecular weight PAO comprising a mixture of oligomers having a number average molecular weight in the range of 120 to 600 and containing a terminal olefin content of at least 25 wt % of total olefinic unsaturation, and b) subsequently contacting at least a portion of said low molecular weight PAO with a Lewis acid catalyst and optionally one or more C4 to C24 alpha olefin monomers to produce a liquid PAO, wherein said liquid PAO has a mass average molecular weight of at least 988.

U.S. Pat. No. 7,104,465B2 relates to a process comprising; contacting i) a monomer comprising a C6 to C20 olefin, ii) a haloaluminate ionic liquid, and iii) a halide component comprising a C1 to C12 organohalide in a reaction zone; and oligomerizing the monomer in the reaction zone to form an oligomer product; wherein the oligomer product has an average molecular weight from 400 to 611 grams/mol, wherein the oligomer product is formed in a presence of less than 8 mol % isoparaffin based upon moles of monomer in the reaction zone, wherein a molar ratio of a halide in the halide component to an aluminum in the haloaluminate ionic liquid is at least 0.14:1, and wherein the oligomer product is formed at a temperature from 15° C. to 125° C.

CN106957677 provides a method for synthesizing low-viscosity PAO4 by high-purity linear alpha olefine through anhydrous AlCl3. The method is characterized in that, in a hot 1-decene monomer, a catalyst is dropwise added, and then low-viscosity PAO4 base oil is synthesized, wherein the catalyst is selected from aluminum chloride anhydrous; the hot 1-decene monomer is heated to 90° C. or above. The invention provides the method for synthesizing the low-viscosity PAO4 by the high-purity linear alpha olefine through the anhydrous $AlCl_3$. The industrial catalyst adopted by the method is low-price; the catalyst is easily obtained; further, the catalyst in a reaction process is easily treated; the reaction condition is mild; the low-viscosity PAO obtained through preparation is good in viscosity temperature characteristic.

U.S. Pat. No. 7,550,640 relates to the use of 1-decene/1-dodecene olefin mixture to produce high viscosity polyalphaolefins (PAOs) having a viscosity of from about 40 cSt to about 100 cSt at 100° C. (ASTM D-445) and a number average molecular weight of between about 1200 to about 4000, particularly useful as lubricant base stocks.

U.S. Pat. No. 7,880,047B2 relates to polyalphaolefins and processes and reaction systems for forming polyalphaolefins from an α-olefin, preferably a C8-C12 α-olefin such as 1-decene, by co-feeding to the polymerization reaction mixture a C8-C12 saturated hydrocarbon, preferably having the same number of carbon atoms as the α-olefin.

U.S. Pat. No. 8,067,652B2 relates to a process for forming a polyalphaolefin, the process comprising the step of polymerizing at least one C8-C12 monomer, preferably a decene such as 1-decene, in the presence of an aluminoxane, an activator and a metallocene to form the polyalphaolefin, wherein the molar ratio of the aluminoxane to the metallocene is less than 250:1.

U.S. Pat. No. 7,259,284B2 relates to a continuous process for the manufacture of high viscosity polyalphaolefin products from an alpha olefin feedstock using an ionic liquid catalyst where the polyalphaolefin products have unique physical properties that make them useful as lubricants or lubricant additives.

U.S. Pat. No. 8,207,390B2 relates to a process to produce poly-alpha-olefins (PAOs) in the presence of a metallocene catalyst with a non-coordinating anion activator and hydrogen.

Still there is need to provide a method of controlling the kinematic viscosity of polyalphaolefins at fixed monomer/aluminum halide mole ratios.

The present invention provides a method of controlling the kinematic viscosity of polyalphaolefins by adjusting the oligomerization temperature at fixed monomer/aluminum halide mole ratios. These newer methods to control kinematic viscosity of polyalphaolefins provide polyalphaolefins with increased stability and mechanical efficiency over a wider range of operating conditions than mineral oil lubricants.

OBJECTIVES OF THE INVENTION

It is a primary objective of the invention which relates to a method of the oligomerization of $C_6$ and above olefin monomer whereby, at a fixed monomer/Al halide mole ratio, polyalphaolefins having desirable kinematic viscosities are prepared by controlling the oligomerization temperature. The oligomerization is carried out in presence of an oligomerizing catalyst comprising of aluminum halide and a promoter, and oligomerizing temperatures of about 10° C. to about 120° C.

Further, an object of the present invention is that the oligomer obtained has Br number is >0.2.

It is a further objective of the present invention to obtain the oligomer with improved viscosity index.

It is a further objective of the present invention to use oligomer as synthetic based oil after hydrogenation and distillation.

SUMMARY OF THE INVENTION

In an aspect of the present invention, the present invention discloses a process for controlling kinematic viscosity of a polyalphaolefin below 70 centistokes, the process comprising the steps of oligomerizing $C_6$ and above olefin monomers in the presence of an aluminum halide, a promoter and optionally, a solvent to obtain a polyalphaolefin; wherein, the kinematic viscosity of the polyalphaolefin is controlled by adjusting oligomerization temperature at a fixed monomer and aluminium halide mole ratio.

In an embodiment of the present invention, the olefin monomer or monomer is selected from the group comprising of 1-decene, 1-dodecene, 1-octene and any mixtures thereof.

In an embodiment of the present invention, mole ratio of the olefin monomer or monomer to the aluminum halide is from 10 to 500, more preferably from 10 to 350, most preferably from 40 to 300.

In an embodiment of the present invention, mole ratio of the aluminum halide to the promoter is from 1 to 10, preferably from 1 to 5.

In an embodiment of the present invention, the promoter is selected from the group/compounds consisting of water, an alcohol, a carboxylic acid, an ester, a ketone, an ether, a halogenated hydrocarbon, or any combination thereof.

In an embodiment of the present invention, the promoter is iso-butyl alcohol.

In an embodiment of the present invention, the olefin monomers or monomers and the solvents have moisture content less than 20 ppm.

In an embodiment of the present invention, the oligomerization temperature is in the range from 10° C. to 150° C.

In an embodiment of the present invention, the oligomerization temperature is 25° C. and 90° C.

In an embodiment of the present invention, residence time during the oligomerization is in the range of 0.5 to 8 hours.

In an embodiment of the present invention, the solvent is selected from C5 to C19 paraffinic hydrocarbons.

In an embodiment of the present invention, conversion from the olefin monomer or monomer to polyalphaolefin is greater than 95%.

In an embodiment of the present invention, the oligomerization comprises C20-24 dimers, C30-36 trimers, C40-48 tetramers, C50-60 pentamers, and C60+ heavies.

DESCRIPTION OF THE INVENTION

The invention relates to a method of the oligomerization of C6 and above olefin monomer whereby, at a fixed monomer/Al halide mole ratio, polyalphaolefins having desirable kinematic viscosities are prepared by controlling the oligomerization temperature. The oligomerization is carried out in presence of an oligomerizing catalyst comprising of aluminum halide and a promoter, and oligomerizing temperatures of about 10° C. to about 120° C.

A method of oligomerization of $C_6$ and above olefin monomer to polyalphaolefin having desirable kinematic viscosity is provided. In an embodiment, the process comprising of the step of oligomerizing in the presence of an aluminum halide and a promoter, wherein the mole ratio of the monomer to the aluminum halide is from 10 to 500, preferably from 10 to 350.

In another embodiment, the invention relates to a process for oligomerization of C6 and above olefin monomer to polyalphaolefin having desirable kinematic viscosity, the process comprising of the step of oligomerizing in the presence of an aluminum halide and a promoter, wherein the aluminum halide is selected from the compounds having the formula as $R_{3-n}AlX_n$ wherein R is a hydrocarbyl group (i.e., an alkyl group), X is a halide and n=0 to 3. In an embodiment, halide can be chloride, bromide or iodide, preferably chloride or bromide. In an embodiment, the aluminum halide is aluminum chloride or aluminum bromide.

In an embodiment, $C_6$ and above olefin monomer can be olefins of the range $C_6$ to $C_{14}$, wherein, mixtures of $C_6$ to $C_{14}$ olefin monomer can be used. In another embodiment, recycle or redistilled olefin monomer can be used.

In an embodiment, the invention relates to a process for oligomerization of and above olefin monomer to polyalphaolefin having desirable kinematic viscosity, the process comprising of the step of oligomerizing in the presence of an aluminum halide and a promoter, wherein the mole ratio of the aluminum halide to the promoter is from 1 to 10, preferably from 1 to 5.

In an embodiment, the promoter is selected from the compounds consisting of water, an alcohol, a carboxylic acid, an ester, a ketone, an ether, a halogenated hydrocarbon, or any combination thereof. In another embodiment, the promoter is selected from the compounds consisting of water, an alcohol, an ester, a ketone or any combination thereof. In an embodiment, the promoter is iso-butyl alcohol.

The inventors were surprised to find that by controlling the oligomerization temperature, at a fixed monomer/Al weight ratio, polyalphaolefins having desirable kinematic viscosities are prepared. In an embodiment, the oligomerization temperature is in the range from 10° C. to 150° C., although temperatures outside this range can be utilized. The preferred oligomerization temperature is 10° C. to 120° C. For non-adiabatic oligomerizations, to maintain steady state conditions, heat transfer capability may be necessary.

Further the inventors were surprised to find that addition of promoter along with the olefin monomer not only improves bromine number of the resultant polyalphaolefin but also controls the exothermicity of the oligomerization. Hence, the reaction proceeds in control manner, leading to lesser probability of hot spots or run away.

In general, the residence time over which the oligomer product is formed is the time where desired conversions are achieved. In an embodiment, the residence time during oligomerization of about 0.5 to 8 h.

For any oligomerizations carried out using aluminium halides, the reactants as well as the apparatus/equipments should be poison free especially air and moisture. Hence for that all the apparatus/equipments are heated and dried either in vacuum or nitrogen while monomers and solvents are distilled, passed through dessicant columns or stored over dessicants. Manipulation before and during oligomerizations for maintaining inert conditions and atmospheres are carried out wherever necessary.

In an embodiment, no solvent is used during the oligomerization. In another embodiment, the choice of solvent can be related to the oligomerization temperature. In an embodiment, the solvent can be selected from $C_5$ to $C_{19}$ paraffinic hydrocarbons.

After the oligomerization is complete, the conversion from the monomer to oligomer is normally greater than 95%. The oligomerization is stopped by addition of water or alcohol, followed by a catalyst removal step, such as an aqueous wash or filtration, absorption or centrifugation. The next step is removal of monomer, promoter and low boiling oligomers through distillation.

The oligomeric product is essentially hydrogenated but can be optionally either before or after distillation. The hydrogenation is carried out using metallic catalyst and hydrogen. Normally, bromine number below 5 and more preferably below 2 will produce an oligomer with excellent oxidation stability. In an embodiment, the resulting product is typically hydrogenated to saturate the oligomers to provide a product having a desired viscosity, for example 40 cSt or 100 cSt at 100° C.

Depending on the viscosity, the product of the oligomerization typically comprises $C_{20-24}$ dimers, $C_{30-36}$ trimers, $C_{40-48}$ tetramers, $C_{50-60}$ pentamers, and $C_{60+}$ heavies.

One of the features of the invention is that the oligomerized product can be used in variety of application for example, as base oils in lubricants, additives for various compositions, viscosity index improvers, dispersants etc.

All monomers and solvents were used as obtained and contained moisture less than 20 ppm. All chemicals based on aluminium halide were handled under nitrogen atmosphere and used as obtained.

$AlCl_3$ based chemistry is extensively used to produce PAO. The variation of reactant mol ratios, effect of varying the substituents or solvents have been extensively studied. In this invention, at fixed monomer/Al mole ratio, by varying the temperature, PAO of different viscosities are prepared. This itself is unique especially for preparing low viscosities PAO as each batch can be tuned to produce, e.g., PAO4 in high concentration. Each batch will produce PAO from dimers to pentamers which can be separated by distillation.

The kinematic viscosity (sometimes also called the momentum diffusivity), defined as the ratio of the viscosity $\mu$ to the density of the fluid $\rho$. It is usually denoted by the Greek letter nu ($\nu$) and has dimension (length)$^2$/time.

SVM 3000 Stabinger Viscometer is used to measure the dynamic viscosity and density of oils and fuels according to ASTM D7042-21. From said dynamic viscosity results/values, the SVM 3000 viscometer automatically calculates the kinematic viscosity and delivers measurement results which are equivalent to ISO 3104 or ASTM D445-19a. The dynamic viscosity is the essential value for evaluating the lubricating behavior.

Viscosity index is a dimensionless number and is used to investigate the change in the viscosity at different temperatures. The greater the viscosity index (VI), the smaller the change in fluid viscosity for a given change in temperature, and vice versa. The viscosity index is calculated from the kinematic viscosity at different temperature ranges.

In an aspect of the present invention, the present invention discloses a process for controlling kinematic viscosity of a polyalphaolefin below 70 centistokes, the process comprising the steps of oligomerizing C6 and above olefin monomers in the presence of an aluminum halide, a promoter and optionally, a solvent to obtain a polyalphaolefin; wherein, the kinematic viscosity of the polyalphaolefin is controlled by adjusting oligomerization temperature at a fixed monomer and aluminium halide mole ratio.

In an aspect of the present invention, the present invention discloses a process for controlling kinematic viscosity of a polyalphaolefin in a range of 1-70 centistokes, the process comprising the steps of: oligomerizing C6 and above olefin monomers in the presence of an aluminum halide, a promoter and optionally, a solvent to obtain a polyalphaolefin; wherein, the kinematic viscosity of the polyalphaolefin is controlled by adjusting oligomerization temperature at a fixed monomer and aluminium halide mole ratio.

According to a feature of the present invention, the olefin monomer or monomer is selected from the group comprising of 1-decene, 1-dodecene, 1-octene and any mixture thereof.

According to a feature of the present invention, mole ratio of the olefin monomer or monomer to the aluminum halide is from 10 to 500, more preferably from 10 to 350, most preferably from 40 to 300.

According to a feature of the present invention, mole ratio of the aluminum halide to the promoter is from 1 to 10, preferably from 1 to 5.

According to a feature of the present invention, the promoter is selected from the group/compounds consisting of water, an alcohol, a carboxylic acid, an ester, a ketone, an ether, a halogenated hydrocarbon, or any combination thereof.

According to a feature of the present invention, the promoter is iso-butyl alcohol.

According to a feature of the present invention, the olefin monomers or monomers and the solvents have moisture content less than 20 ppm.

According to a feature of the present invention, the oligomerization temperature is in the range from 10° C. to 150° C.

According to a feature of the present invention, the oligomerization temperature is 25° C. and 90° C.

According to a feature of the present invention, residence time during the oligomerization is in the range of 0.5 to 8 hours.

According to a feature of the present invention, the solvent is selected from C5 to C19 paraffinic hydrocarbons.

According to a feature of the present invention, conversion from the monomer to polyalphaolefin is greater than 95%.

According to a feature of the present invention, the oligomerization comprises C20-24 dimers, C30-36 trimers, C40-48 tetramers, C50-60 pentamers, and C60+ heavies.

According to a feature of the present invention, the kinematic viscosity decreases on increasing the monomer and the aluminium halide mole ratio.

In another aspect of the present invention, the present invention discloses a process for preparing a polyalphaolefin, the process comprising the steps of: a) oligomerizing one or more alpha olefin monomers having C6-C14 carbon atoms under an inert atmosphere in the presence of an aluminum halide, a promoter and optionally, a solvent to obtain an oligomeric product in a reaction mass; wherein the aluminum halide is selected from the compounds having the formula as $R_{3-n}AlX_n$; wherein R is a hydrocarbyl group or an alkyl group, X is a halide, and n=0 to 3; wherein the halide is selected from chloride or bromide; b) stopping the oligomerization of the monomers in the reaction mass by addition of water or alcohol; c) removing the aluminum halide from the reaction mass by aqueous wash or filtration or absorption or centrifugation or any combination thereof; d) separating unconverted monomer, the promoter and the oligomeric product from the reaction mass through distillation; e) hydrogenating the oligomeric product to saturate oligomers to provide polyalphaolefin; wherein kinematic viscosity of the polyalphaolefin is below 70 centistokes.

In another aspect of the present invention, the present invention discloses a process for preparing a polyalphaolefin, the process comprising the steps of a) oligomerizing C6 and above olefin monomers under an inert atmosphere in the presence of an aluminum halide, a promoter and optionally, a solvent to obtain an oligomeric product in a reaction mass; wherein the aluminum halide is selected from the compounds having the formula as $R_{3-n}AlX_n$; wherein R is a hydrocarbyl group or an alkyl group, X is a halide, and n=0 to 3; wherein the halide is selected from chloride or bromide; b) stopping the oligomerization of the monomers in the reaction mass by addition of water or alcohol; c) removing the aluminum halide from the reaction mass by aqueous wash or filtration or absorption or centrifugation or any combination thereof; d) separating unconverted monomer, the promoter and the oligomeric product from the reaction mass through distillation; e) hydrogenating the oligomeric product to saturate oligomers to provide polyalphaolefin; wherein kinematic viscosity of the polyalphaolefin is below 70 centistokes.

In a feature of the present invention, the hydrogenation is carried out using metallic catalyst and hydrogen.

In a feature of the present invention, conversion from the monomer to oligomer is greater than 95%.

In another aspect of the present invention, the present invention discloses a process for preparing a polyalphaolefin, the process comprising the steps of a) oligomerizing C6 and above olefin monomers under an inert atmosphere in the presence of an aluminum halide, a promoter and optionally, a solvent to obtain an oligomeric product, i.e., polyalphaolefin; wherein kinematic viscosity of the polyalphaolefin is below 70 centistokes.

Table 1 showing the effect of temperature on the viscosity of the PAO at fixed Monomer/Al ratios

| | KV@100° C. | | |
|---|---|---|---|
| Monomer/Al ratio | Oligomerization Temp 25° C. | Oligomerization Temp 90° C. | % Conversion |
| 10 | 61.1 | 30.9 | 95 |
| 25 | 60.1 | 30.2 | 97 |
| 48 | 53.9 | 25.4 | 98 |
| 83 | 45.6 | 23.6 | 98 |
| 100 | 30.4 | 8.1 | 96 |
| 165 | 23.4 | 5.8 | 96 |
| 282 | 12.1 | 4.5 | 95 |
| 450 | 8.6 | 3.2 | 96 |

Table 2 showing the effect of fixing the Monomer/Al ratios during runaway reaction

| | KV@100° C. | | |
|---|---|---|---|
| Monomer/Al ratio | Oligomerization Temperature 25° C. | Runaway Reaction Temperature 100-110° C. | % Conversion |
| 10 | 61.1 | 12.9 | 95 |
| 83 | 45.6 | 10.9 | 98 |
| 100 | 30.4 | 6.5 | 96 |
| 165 | 23.4 | 4.0 | 96 |
| 282 | 12.1 | 2.1 | 95 |

EXAMPLES

The present invention is exemplified by following non-limiting examples:

Example 1

In 2 L CSTR, 250 ml of hexane, 13.6 g of AlCl$_3$ (0.10 mol) and 4.0 mL iso-butanol was added and stirred for 15 min. The oligomerization temperature was set to 25° C. Addition of 1-decene (C10/AlCl$_3$ mol ratio=83) was started at flow rate of 8.4 ml/min for 3 hours. After complete addition of monomer, the solution was kept on stirring for additional 1 hour. 100 ml of deionized water was added to quench the reaction followed by another water washing. The subsequent oil obtained was kept on sodium sulphate overnight and filtered. After removal of monomer, the oil was hydrogenated using Nickel on Kieselguhr catalyst. The hydrogenated oil had KV of 45.6 cSt@100° C., VI of 147.

Example 2

The procedure for oligomerization followed was same as described in Example 1 but instead, the oligomerization temperature was set to 90° C. The hydrogenated oil had KV of 23.5 cSt@100° C., VI of 147.

Example 3

The procedure for oligomerization followed was same as described in Example 1 but instead, the C10/AlCl$_3$ mol ratio was kept as 282. The hydrogenated oil had KV of 12.1 cSt@100° C., VI of 142.

Example 4

The procedure for oligomerization followed was same as described in Example 1 but instead, the C10/AlCl$_3$ mol ratio was kept as 282 and the oligomerization temperature was set to 90° C. The hydrogenated oil had KV of 4.5 cSt@100° C., VI of 142.

Example 5

The procedure for oligomerization followed was same as described in Example 1 but instead, the C10/AlCl$_3$ mol ratio was kept as 165. The hydrogenated oil had KV of 23.4 cSt@100° C., VI of 142.

Example 6

The procedure for oligomerization followed was same as described in Example 1 but instead, the C10/AlCl$_3$ mol ratio was kept as 165 and the oligomerization temperature was set to 90° C. The hydrogenated oil had KV of 5.8 cSt@100° C., VI of 144.

Example 7

The procedure for oligomerization followed was same as described in Example 1 but instead, the C10/AlCl$_3$ mol ratio was kept as 100. The hydrogenated oil had KV of 30.4 cSt@100° C., VI of 142.

Example 8

The procedure for oligomerization followed was same as described in Example 1 but instead, the C10/AlCl$_3$ mol ratio was kept as 100 and the oligomerization temperature was set to 90° C. The hydrogenated oil had KV of 8.1 cSt@100° C., VI of 141.

Example 9

The procedure for oligomerization followed was same as described in Example 1 but instead, the monomer/AlCl$_3$ mol ratio was kept as 48 and the monomer was 1-dodecene. The hydrogenated oil had KV of 53.9 cSt@100° C., VI of 147.

Example 10

The procedure for oligomerization followed was same as described in Example 1 but instead, the monomer/AlCl$_3$ mol ratio was kept as 48 and the monomer was 1-dodecene, and the oligomerization temperature was set to 90° C. The hydrogenated oil had KV of 25.4 cSt@100° C., VI of 142.

TECHNICAL ADVANTAGES OF THE INVENTION

The present invention has the following advantage over the prior arts:
  Using fixed monomer/Al ratios, can control viscosity of the resultant PAO by varying the temperature.
  Particularly, useful advantage in low viscosity PAO preparation where any variation in catalyst amount would not lead to batch failure.
  Addition of promoter to the feed controls the exotherm during the oligomerization.

We claim:

1. A process for controlling kinematic viscosity of a polyalphaolefin in a range of 1-70 centistokes at 100° C., the process comprising:
  oligomerizing C6 and above olefin monomers in presence of an aluminium halide, a promoter, and a solvent to obtain the polyalphaolefin; wherein the promoter is water, an alcohol, a ketone, an ether, or any combination thereof;
  wherein the kinematic viscosity of the polyalphaolefin is controlled by adjusting oligomerization temperature at a fixed mole ratio of olefin monomer and the aluminium halide, and wherein the mole ratio of the olefin monomer to the aluminium halide is from 10 to 500.

2. The process as claimed in claim 1, wherein the olefin monomer is selected from the group consisting of 1-decene, 1-dodecene, 1-octene and a mixture thereof.

3. The process as claimed in claim 1, wherein a mole ratio of the aluminium halide to the promoter is from 1 to 10.

4. The process as claimed in claim 1, wherein the promoter is iso-butyl alcohol.

5. The process as claimed in claim 1, wherein the olefin monomers and the solvent have a moisture content less than 20 ppm.

6. The process as claimed in claim 1, wherein an oligomerization temperature is in a range from 10° C. to 150° C.

7. The process as claimed in claim 1, wherein the oligomerization temperature is in a range of 25° C. and 90° C.

8. The process as claimed in claim 1, wherein a residence time during the oligomerization is in a range of 0.5 to 8 hours.

9. The process as claimed in claim 1, wherein the solvent is selected from C5 to C19 paraffinic hydrocarbons.

10. The process as claimed in claim 1, wherein a conversion from the monomer to the polyalphaolefin is in a range of 95% to 98%.

11. The process as claimed in claim 1, wherein the oligomerizing C6 and above olefin monomers produces C20-24 dimers, C30-36 trimers, C40-48 tetramers, C50-60 pentamers, and C60+ heavies.

* * * * *